(12) United States Patent
Anderson

(10) Patent No.: US 7,744,623 B2
(45) Date of Patent: *Jun. 29, 2010

(54) VESSEL OCCLUSION CLAMP

(75) Inventor: Steven R. Anderson, Las Flores, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 654 days.

This patent is subject to a terminal disclaimer.

(21) Appl. No.: 11/184,174

(22) Filed: Jul. 18, 2005

(65) Prior Publication Data

US 2005/0251184 A1 Nov. 10, 2005

Related U.S. Application Data

(63) Continuation of application No. 10/129,517, filed on May 3, 2002, now Pat. No. 6,932,825.

(60) Provisional application No. 60/168,943, filed on Dec. 3, 1999.

(51) Int. Cl.
*A61B 17/00* (2006.01)
(52) U.S. Cl. .................................................. 606/207
(58) Field of Classification Search ............. 606/51–52, 606/120, 139, 144, 148–150, 157, 205–211, 606/158; 24/507, 521, 564; 81/418, 419, 81/424.5, 426; D24/143; D8/52, 54
See application file for complete search history.

(56) References Cited

U.S. PATENT DOCUMENTS

| | | | |
|---|---|---|---|
| 3,503,397 A * | 3/1970 | Raible et al. | ................. 606/207 |
| 3,746,002 A | 7/1973 | Heller | |
| 5,342,381 A | 8/1994 | Tidemand | |

(Continued)

FOREIGN PATENT DOCUMENTS

WO    WO 99/11179    3/1999

(Continued)

OTHER PUBLICATIONS

European Patent Office, European Supplementary Search Report, for 00992821.9-2318, PCT/US0042390 mailed Mar. 15, 2006. Supplementary Partial European Search Report.

*Primary Examiner*—Todd E Manahan
*Assistant Examiner*—Jennifer L Hornberger
(74) *Attorney, Agent, or Firm*—Patrick Y. Ikehara; David G. Majdali; Cynthia A. Bonner

(57) ABSTRACT

A surgical clamp for occluding a body conduit includes first and second jaws moveable relative to each other in a generally parallel relationship. A handle assembly is operable to move the jaws relative to each other between a space position and proximate position. The first jaw has an elongate configuration characterized by a length and a width. First portions of the first jaw have in cross section a first shape which remains generally constant in area along the first jaw, while second portions have in cross section a second shape which varies in area along the length of the first jaw. The resulting clamp has a low profile jaw design which dimensional-shaped cross section which provide increased stiffness and reduced flexibility.

17 Claims, 4 Drawing Sheets

U.S. PATENT DOCUMENTS

| | | | |
|---|---|---|---|
| 5,396,900 A | | 3/1995 | Slater et al. |
| 5,591,182 A | | 1/1997 | Johnson |
| 5,833,697 A | * | 11/1998 | Ludwick ..................... 606/147 |
| 6,228,104 B1 | * | 5/2001 | Fogarty et al. .............. 606/207 |

FOREIGN PATENT DOCUMENTS

| | | |
|---|---|---|
| WO | WO-99/30623 A | 6/1999 |
| WO | WO-00/78235 A | 12/2000 |

\* cited by examiner

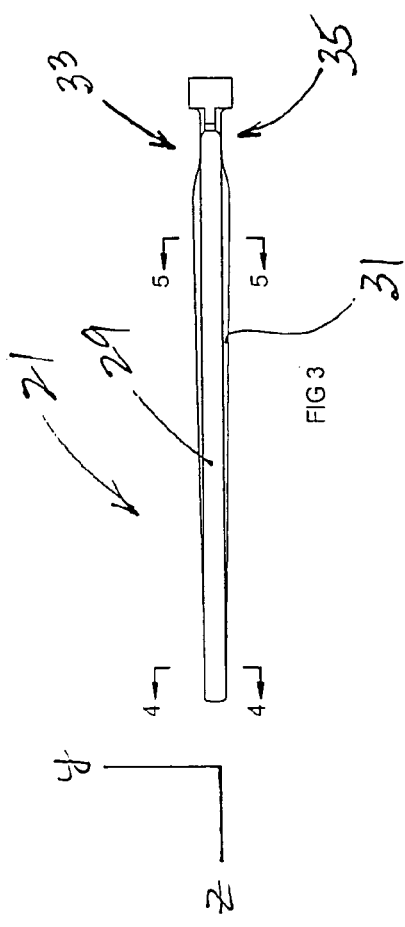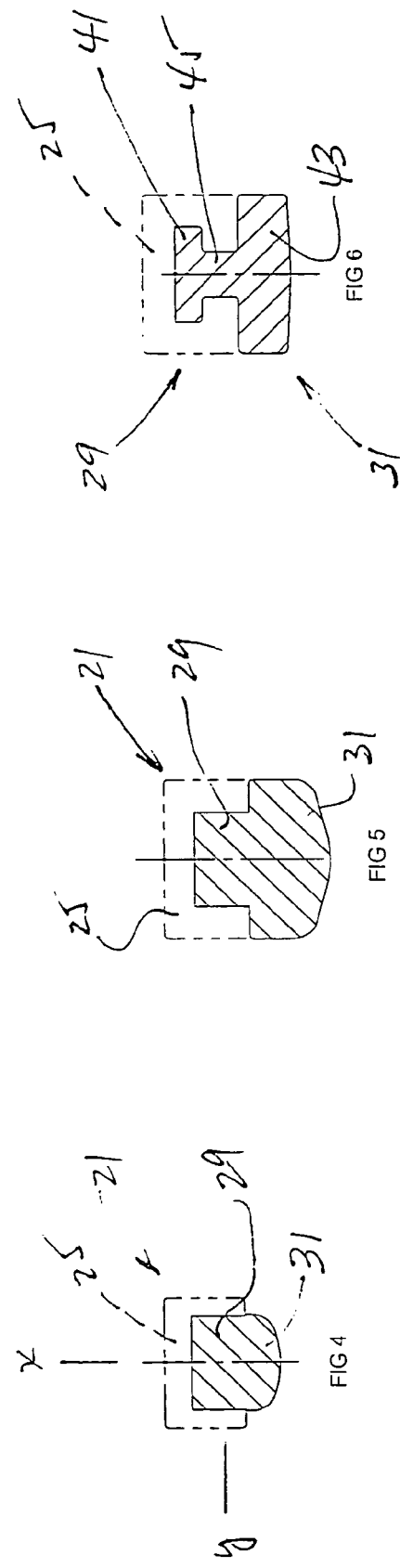

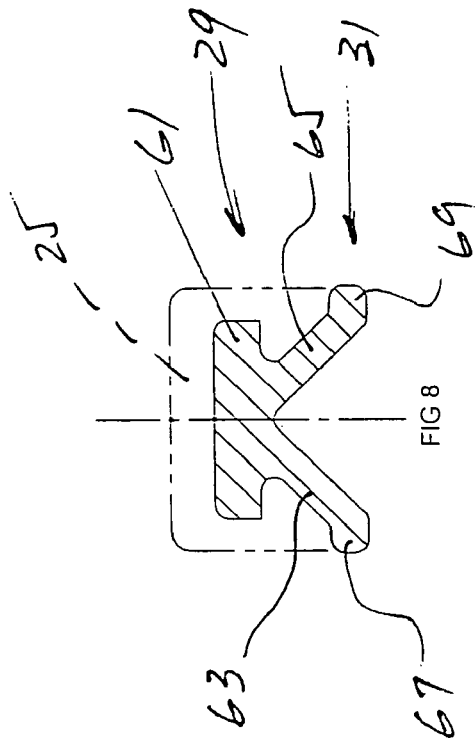
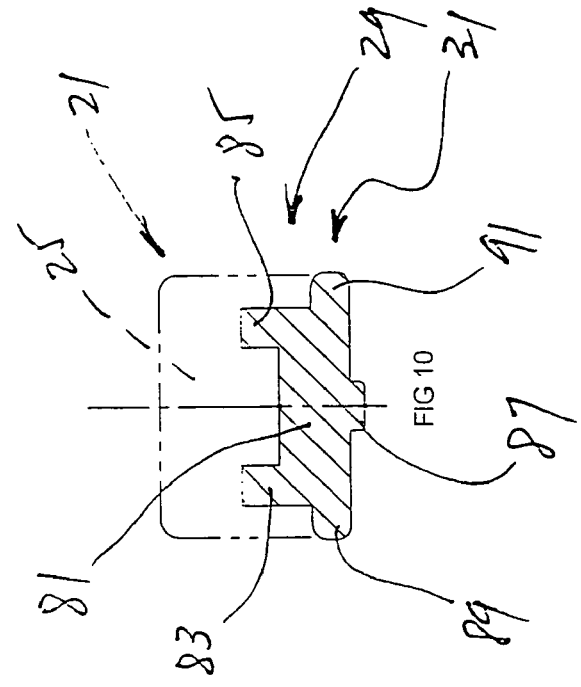
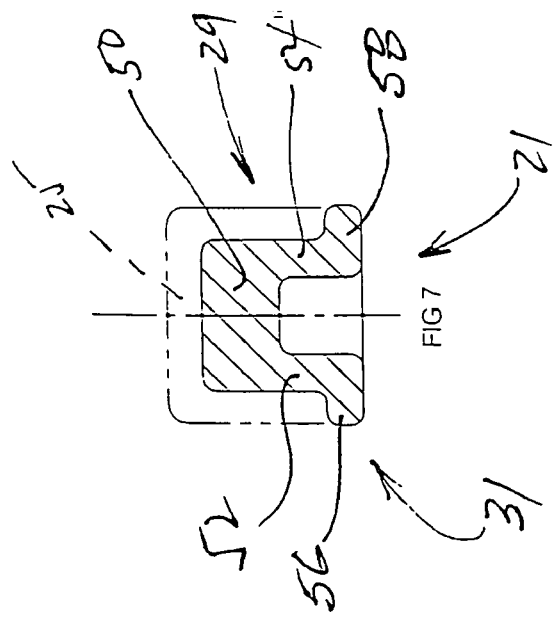
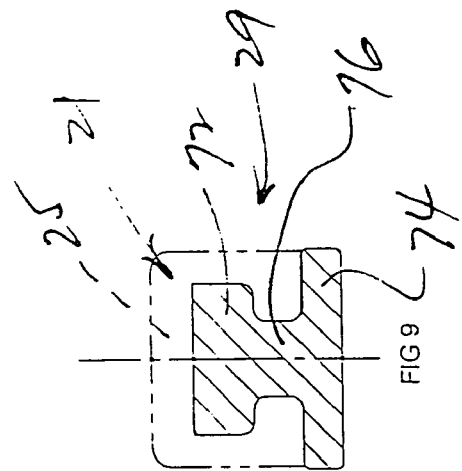

VESSEL OCCLUSION CLAMP

CROSS-REFERENCE TO RELATED APPLICATIONS

This application is a continuation of U.S. patent application Ser. No. 10/129,517, filed on May 3, 2002, now U.S. Pat. No. 6,932,825 which claims benefit of U.S. Provisional Patent Application No. 60/168,943, filed Dec. 3, 1999, the disclosures of which are hereby incorporated by reference as if set forth in full herein.

BACKGROUND OF THE INVENTION

1. Field of the Invention

This invention relates generally to surgical clamps, and more specifically to blood vessel occlusion clamps.

2. Discussion of the Prior Art

Surgical occlusion clamps are commonly used to close off or occlude body conduits, such as blood vessels. A common variety of vessel occlusion clamp is that referred to as a "Bahnson" clamp, which has small metal handles that operate a pair of opposing jaws. When the jaws are brought into close proximity on either side of a vessel, the vessel is squeezed against itself to achieve at least partial occlusion. It is of particular importance that the jaws of the clamp be stable, and sufficiently inflexible that the jaws do not cross over or scissor, but rather press directly against each other along their length to occlude any conduit disposed between the jaws.

It is also desirable to have a thin, low-profile jaw design that can access narrow areas. In the past, this desire for a low-profile design has worked against the need for stability in the jaws. Jaw inserts have been provided, but typically have had exposed edges, ends, and corners, which tend to entrap or entangle surgical sutures.

SUMMARY OF THE INVENTION

In accordance with the present invention, a vessel occlusion clamp of the Bahnson type is provided with improved stability and reduced flexibility, while maintaining a low-profile jaw design. In a preferred embodiment of the clamp, the jaws are provided with a receding or tapered T-beam cross section, which greatly reduces the bendibility or flexibility of the jaws. Other dimensional-shaped cross sections of interest include a U-beam cross section, an I-beam cross section, a trapezoidal I-beam cross section, a continuous or whole-length T-beam cross section, a B-channel cross section, and an L-beam cross section. With the dimensional-shaped, cross section design, beam stiffness is substantially increased, while transverse deflection is greatly reduced. In addition, the transverse members forming the beam cross sections can be relied on to provide shielding of the jaw insert edges. This shielding prevents entrapment or entanglement of surgical sutures. Scallops or hollowed recesses can be provided in the jaws to facilitate installation and removal of the inserts without degrading structural jaw stability.

In one aspect of the invention a surgical clamp is adapted for use in occluding a body conduit. The clamp includes a first jaw, and a second jaw movable relative to the first jaw in a generally parallel relationship. A handle assembly is operable to move the first and second jaws relative to each other between a spaced position and a proximate position. The first jaw has an elongate configuration characterized by a length and a width. First portions of the first jaw have in radial cross section a first shape which remains generally constant in area along the length of the first jaw. Second portions of the first jaw have in cross section a second shape which changes in area along the length of the first jaw. The first portions will typically have a first width while the second portions will have a second width greater than the first width. An insert is adapted to be removably mounted on the first portions with the second portions extending laterally of the insert.

In a further aspect of the invention, the surgical clamp includes a handle assembly and a pair of opposing jaws movable by the handle assembly in a plane of operation between a spaced orientation, wherein the jaws are spread to recede the body conduit, and a proximal orientation wherein the jaws are substantially closed to occlude the body conduit. At least one of the jaws has in cross section a non-rectangular configuration. An insert having a first width is carried by first portions of the jaw which have a second width. Second portions of the jaw have a third width which defines with the first portions the thickness of the jaw. The first width of the insert is less than the third width of the second portions and greater than the second width of the first portions.

These and other features and advantageous of the invention will be better understood with a description of preferred embodiments and reference to the associated drawings.

DESCRIPTION OF THE DRAWINGS

FIG. 3 is a side-elevation view of a clamp jaw illustrating a tapered, T-beam cross section;

FIG. 4 is a cross section view taken along lines A-A of FIG. 3;

FIG. 5 is a cross section view taken along lines B-B of FIG. 3;

FIG. 6 is a cross section view similar to FIG. 5 and illustrating a trapezoidal I-beam cross section;

FIG. 7 is a cross section view similar to FIG. 5 and illustrating a U-channel cross section;

FIG. 8 is a cross section view similar to FIG. 5 and illustrating a V-beam cross section;

FIG. 9 is a cross section view similar to FIG. 5 and illustrating an I-beam cross section; and FIG. 10 is a cross section view similar to FIG. 5 and illustrating an L-beam cross section.

DESCRIPTION OF PREFERRED EMBODIMENT

Figure 1:
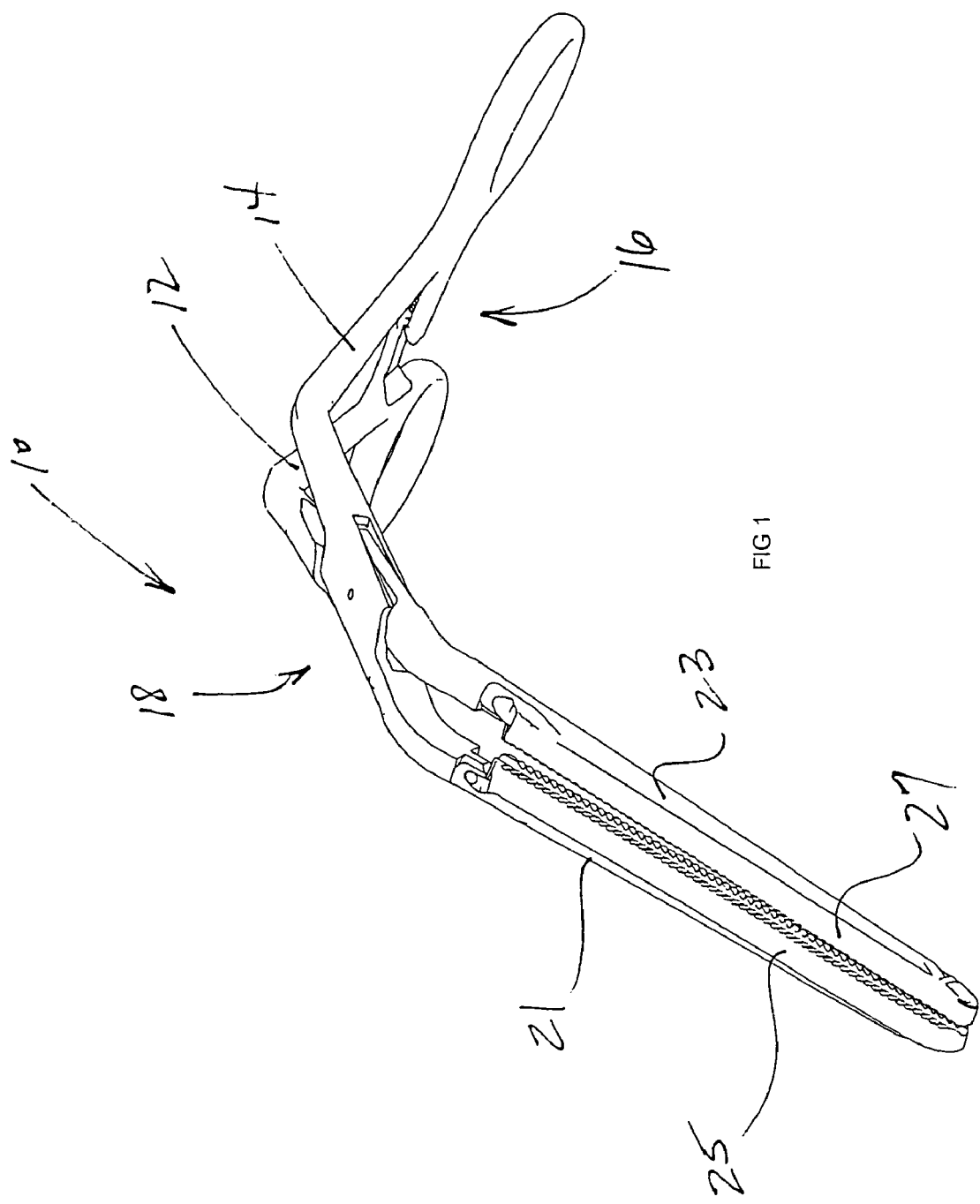
FIG. 1 is a front side perspective view of a vessel occlusion clamp of the Bahnson type, illustrating disposable inserts mounted on parallel jaws having a dimensional-shaped, cross section design.
Figure 2:
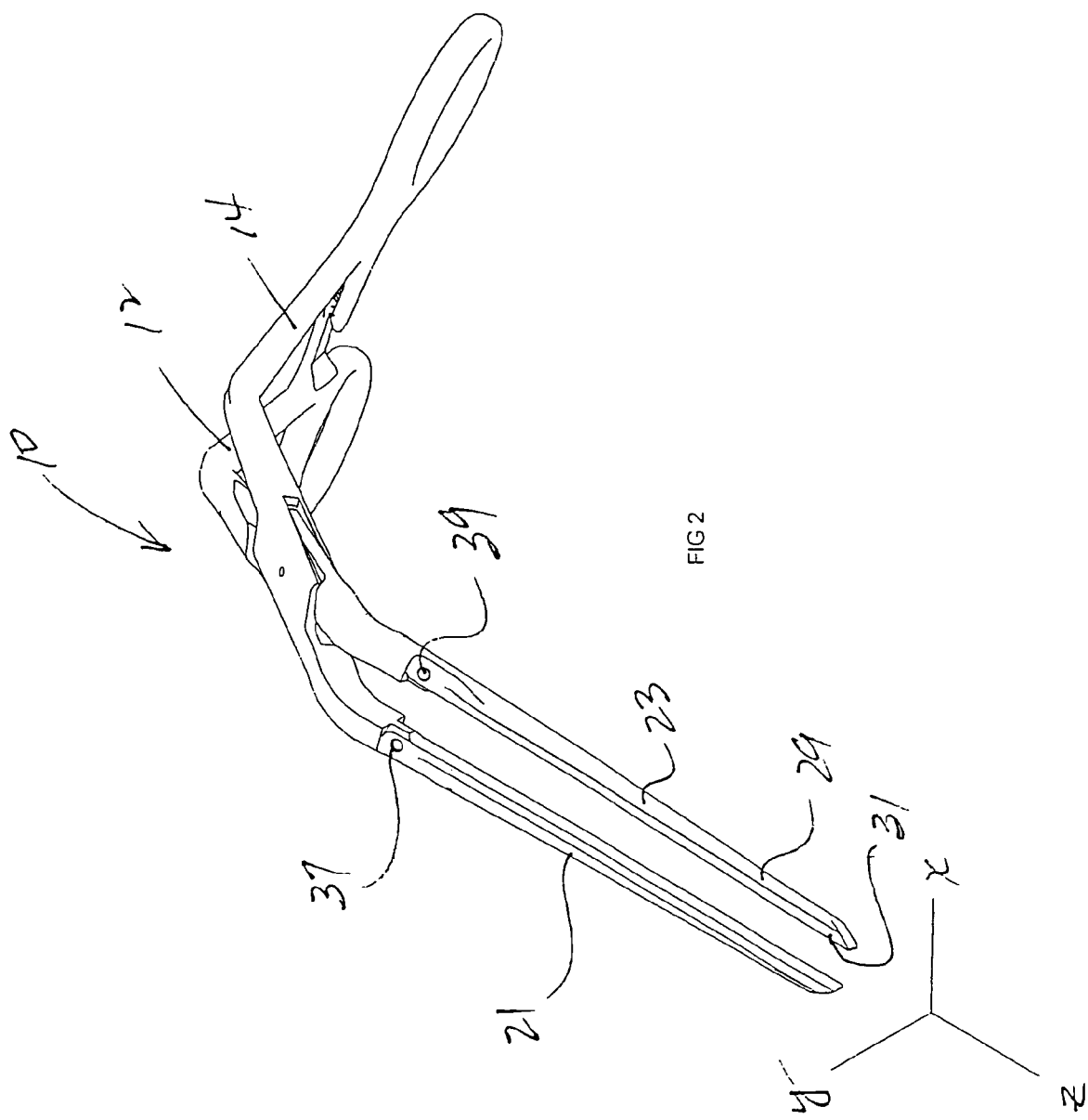
FIG. 2 is a perspective view similar to FIG. 1, showing the jaws with the disposable inserts removed.

A vascular occlusion clamp of the Bahnson type is illustrated in FIG. 1 and designated generally by the referenced numeral 10. The clamp 10 includes a pair of handles 12 and 14 with a ratchet lock 16, which pivot on a fulcrum 18 to move jaws 21 and 23 in a generally parallel relationship. Disposable inserts 25 and 27 are removably mounted on the associated jaws 21, 23. In FIG. 2, the inserts 25 and 27 have been removed in order to illustrate the dimensional-shaped design of the jaws 21 and 23. From this view it can be seen that the jaws 21 and 23 extend along a Z axis but move generally along an X axis. The width of the jaws is measured along a Y axis. Thus the jaws having a length along the Z axis, a width along the Y axis, and a thickness along the X axis.

This dimensional-shaped design is further illustrated in the side-elevation view of FIG. 3 and the associated cross sectional views of FIGS. 4 and 5. The side elevation view of FIG. 3 is drawn in the YZ plane while the cross sectional views of FIGS. 4 and 5 are drawn in the XY plane. In all of the cross sectional views of FIGS. 4-10, a preferred disposition of the associated insert 25 is illustrated in dotted lines.

In this embodiment, the jaw 21 has an engagement section 29 with a generally constant profile along its length. This engagement section 29 is intended to occupy a channel within the associated insert 25. The jaw 21 also includes a support section 31 which, in cross section forms a T with the elongate section 29. It is this support section 31 that provides this embodiment with its dimensional-shaped structure. In this case, the support section 31 tapers from a narrow width at the distal end of the jaw 21 to a maximum width near the proximal end of the jaw 21. With this dimensional-shaped configuration, the cross section of the jaw 21 is provided with substantially increased beam stiffness along the X axis and reduced transverse deflection along the Y axis.

The support section 31 can also be relied on to shield the edges, ends, and corners of the insert 25 that can entrap or entangle surgical sutures. With the shielding provided by these transverse elements, the edges, ends, and corners are not as prominent. While this prevents entrapment of surgical sutures, it can also make it more difficult to remove the inserts 25 and 27 for disposal. It is for this reason that the embodiment of FIG. 3 is provided with scallops or hollow recesses 33 and 35, which provide shallow access to a proximal edge of each insert. With these recesses 33 and 35 provided in proximity to counterbored pin recesses 37, 39 (FIG. 2), the inserts 25 and 27 can be easily engaged and removed.

Other dimensional-shaped cross sectional designs providing these advantages are illustrated in FIGS. 6-10. Each of these non-rectangular shaped cross sections provide increased beam stiffness and reduce transverse deflection, compared to the rectangular cross sections of prior designs.

In the embodiment of FIG. 6, the jaw 21 has a trapezoidal I-beam shape characterized by an inner flange 41 joined to an outer flange 43 by a center flange 45. In this case, the inner flange 41 and the center flange 45 formed the engagement section 29 which is disposed in the channel of the insert 25. The outer flange 43 forms the support section 31 and maintains an abutting relationship with the insert 25. This I-beam shape has a trapezoidal configuration in that the inner flange 41 has a width less than the outer flange 43.

In the embodiment of FIG. 7, the jaw 21 in cross section has a generally U-shaped configuration. A center flange 50 is supported by two side flanges 52 and 54 which extend to outwardly directed flanges 56 and 58 respectively. In this embodiment, the center flange 50 and side flanges 52 and 54 form the engagement section 29 while the outwardly directed flanges 56 and 58 form the support section 31. As in previously embodiments, the engagement section 29 is received within a center channel of the insert 25 while the support section 31 is disposed in an abutting relationship with the insert 25.

The embodiment of FIG. 8 includes a jaw 21 having in cross section a V-shaped configuration. This embodiment includes a top flange 61 supported by side flanges 63 and 65 which extend to outwardly directed flanges 67 and 69, respectively. In this embodiment, the side flanges 63 and 65 are disposed at an acute angle with respect to the top flange 61 and are also disposed at an angle with respect to each other. The top flange 61 and side flanges 63 and 65 form the engagement section 29 and are adapted to be disposed within a channel of the insert 25. The outwardly directed flanges 67 and 69 form the support section 31 and are disposed in an abutting relationship with the insert 25.

The embodiment of FIG. 9 includes a jaw 21, having in cross section an I-Beam shape similar to that of FIG. 6. Thus, the jaw 21 has a top flange 72, joined to a bottom flange 74 by a center flange 76. In this embodiment, the top flange 72 has the same width as the bottom flange 74, but a greater thickness than the bottom flange 74. Also, the flanges 72, 74 and 76 are all disposed within the channel of the insert 25. Accordingly, these three flanges in the illustrated embodiment form the engagement section 29 of the jaw 21.

In the embodiment of FIG. 10, the jaw 21 in cross section has a U-shaped configuration. This embodiment is characterized by a bottom flange 81, side flanges 83 and 85, and a center flange 87. The side flanges 83 and 85 are equally spaced from the bottom flange 87 and extend from a side of the bottom flange 81, opposite to that of the center flange 87. Outwardly directed flanges 89 and 91 extend from the bottom flange 81 outwardly of the side flanges 83 and 85. In this embodiment, portions of the bottom flange 81 together with the side flanges 83 and 85 form the engagement section 29. The remaining portions of the bottom flange 81 together with the outwardly directed flanges 89 and 91 and the bottom flange 87 form the support section 31.

The resulting clamp 10 maintains the desired low profile jaw design, while the dimensional-shaped cross sections provide increased stiffness and reduced flexibility. As a result, transverse deflection is substantially avoided. The dimensional-shaped cross section also provides shielding to prevent entanglement of surgical sutures, while the scalloped and hollowed recessed 33 and 35 facilitate removal of the inserts 25 and 27.

Many alterations and modifications can be made to the foregoing preferred embodiments without departing from the spirit and scope of the invention. Therefore it must be understood that the illustrated embodiments have been set forth only by way of example, and should not be taken as limiting the invention. For example, notwithstanding the fact that the claims set forth below recite certain elements and combinations, it must be expressly understood that the invention includes other combinations of fewer, more or different elements, which are not disclosed above even when not initially claimed in such combinations.

In addition, the words used in this specification to describe the invention and its various embodiments are to be understood not only in the sense of their commonly defined meanings, but also in the sense of any special definitions used in this specification, which may extend beyond the scope of the commonly defined meanings. Thus if an element can be understood in the context of this specification as including more than one meaning, than its use in the claims must be understood as being generic to all possible meanings supported by the specification and by the word itself.

The definitions of the words or elements of the following claims are, therefore, defined in the specification to include not only the combination of the elements which are literally set forth, but all equivalent structure, material or method steps for performing substantially the same function, in substantially the same way, to obtain substantially the same way to obtain substantially the same result. In this sense it is therefore contemplated that an equivalent substitution of two or more elements may be made for any one of the elements in the claims below or that a single element may be substituted for two or more elements in a claim.

Insubstantial changes from the claimed subject matter, now known or later devised, are expressly contemplated as being equivalently within the scope of the claims. Therefore, obvious substitutions now or later known to one with ordinary skill in the art are deemed to be within the scope of the defined elements.

The claims are thus to be understood to include what is specifically illustrated and described above, what is conceptually equivalent, what can be obviously substituted, and also what essentially incorporates the idea of the invention. Many alterations and modifications can be made to the foregoing preferred embodiments without departing from the spirit and scope of the invention. Therefore it must be understood that the illustrated embodiments have been set forth only by way of example, and should not be taken as limiting the invention. For example, notwithstanding the fact that the claims set forth below recite certain elements and combinations, it must be expressly understood that the invention includes other combinations of fewer, more or different elements, which are not disclosed above even when not initially claimed in such combinations.

In addition, the words used in this specification to describe the invention and its various embodiments are to be understood not only in the sense of their commonly defined meanings, but also in the sense of any special definitions used in this specification, which may extend beyond the scope of the commonly defined meanings. Thus if an element can be understood in the context of this specification as including more than one meaning, than its use in the claims must be understood as being generic to all possible meanings supported by the specification and by the word itself.

The definitions of the words or elements of the following claims are, therefore, defined in the specification to include not only the combination of the elements which are literally set forth, but all equivalent structure, material or method steps for performing substantially the same function, in substantially the same way, to obtain substantially the same way to obtain substantially the same result. In this sense it is therefore contemplated that an equivalent substitution of two or more elements may be made for any one of the elements in the claims below or that a single element may be substituted for two or more elements in a claim.

Insubstantial changes from the claimed subject matter, now known or later devised, are expressly contemplated as being equivalently within the scope of the claims. Therefore, obvious substitutions now or later known to one with ordinary skill in the art are deemed to be within the scope of the defined elements.

The claims are thus to be understood to include what is specifically illustrated and described above, what is conceptually equivalent, what can be obviously substituted, and also what essentially incorporates the idea of the invention.

The invention claimed is:

1. A surgical clamp for occluding the body conduit comprising:
   a first jaw;
   a second jaw moveable relative to the first jaw;
   a handle assembly operable to move the first jaw and the second jaw relative to each other between a spaced position and a proximate position;
   the first jaw having an elongate configuration characterized by a length along a Z-axis, a width along a Y-axis, and a thickness along an X-axis, wherein the jaw extends along the Z-axis but moves between the spaced position and the proximate position along the X-axis, and the Y-axis is perpendicular to both the X-axis and the Z-axis;
   first portions of the first jaw having a first width and having in cross section a first shape which remains generally constant in area along the length of the first jaw;
   a removable insert mounted on the first portions of the first jaw; and
   second portions of the first jaw having a second width greater than the first width and arranged under the first portions having in cross section a second shape which changes in area along the length of the first jaw, the first and second widths being disposed along the Y-axis.

2. The surgical clamp recited in claim 1 wherein the second portions of the first jaw are disposed outwardly of the first portions of the first jaw.

3. The surgical clamp recited in claim 1, wherein:
   the first and second portions are integrally formed into a beam having in radial cross section a non-rectangular shape.

4. The surgical clamp recited in claim 1, wherein:
   the first jaw is configured to have a pivotal relationship with the insert at the distal end; and
   the first jaw is configured to have a snap-fit relationship with the insert at the proximal end.

5. The clamp of claim 1 wherein the first portion of the first jaw has a first surface extending lengthwise along the first portion of the first jaw and the second portion of the first jaw has a second surface extending lengthwise along the second portion of the first jaw, the second surface being disposed farther from the second jaw than the first surface.

6. The clamp of claim 1, wherein the insert has a first surface area and the first portion has a second surface area, the first surface area being greater than the second surface area of the first portion.

7. The clamp of claim 1, wherein the insert has a generally uniform width throughout the length of the first jaw, the width of the insert being greater than the width of the first portion.

8. The clamp of claim 1, wherein the handle assembly is disposed along a first axis and the first and second jaws are disposed along a second axis traverse to the first axis.

9. A surgical clamp for occluding a body conduit, comprising:
   a handle assembly;
   a pair of opposing jaws movable by the handle assembly in a plane of operation along an X-axis between a spaced orientation wherein the jaws are spread to receive the body conduit, and a proximate orientation wherein the jaws are substantially closed to occlude the body conduit;
   a removable insert having a first width;
   at least one of the jaws having in radial cross section a non-rectangular shape and including a first longitudinal portion and a second longitudinal portion;
   the first portion of the jaw having a length and a generally uniform second width along the length of the first portion and being sized and configured to receive the insert;
   the second portion of the jaw having a third width and defining with the first portion the thickness of the jaw; and
   the first width of the insert being less than the width of the second longitudinal portions and greater than the second width of the first longitudinal portions of the jaw, the first, second and third widths all disposed along a Y-axis, the Y-axis being perpendicular to the X-axis.

10. The surgical clamp recited in claim 9, wherein the insert has a longitudinal channel and is carried by at least one jaw;
    the first portion being disposed within the longitudinal channel of the insert; and
    the second portion being disposed adjacent to the insert.

11. The surgical clamp recited in claim 10, wherein:
    the second portion is disposed in an abutting relationship with the insert.

12. The surgical clamp recited in claim 9, wherein:
the first and the second portions integrally form a structural beam having in radial cross section a shape that is non-rectangular.

13. The surgical clamp recited in claim 12 wherein the structural beam is one of a trapezoidal beam, a U-beam, a V-beam, an I-beam, a T-beam and an L-beam.

14. The clamp of claim 9, wherein the first portion has a first surface extending lengthwise along the first portion and the second portion has a second surface extending lengthwise along the second portion, the second surface being disposed farther from the other jaw than the first surface.

15. The clamp of claim 9, wherein the insert has a first surface area and the first portion has a second surface area, the first surface area being greater than the second surface area.

16. The clamp of claim 9, wherein the handle assembly is disposed along a plane of operation that is traverse to the plane of operation of the jaws.

17. The clamp of claim 9, wherein the jaws are orientated generally orthogonal to the handle assembly.

* * * * *